March 19, 1974 W. H. JESSEL, JR., ET AL Plant Pat. 3,527
CHRYSANTHEMUM PLANT
Filed June 19, 1972
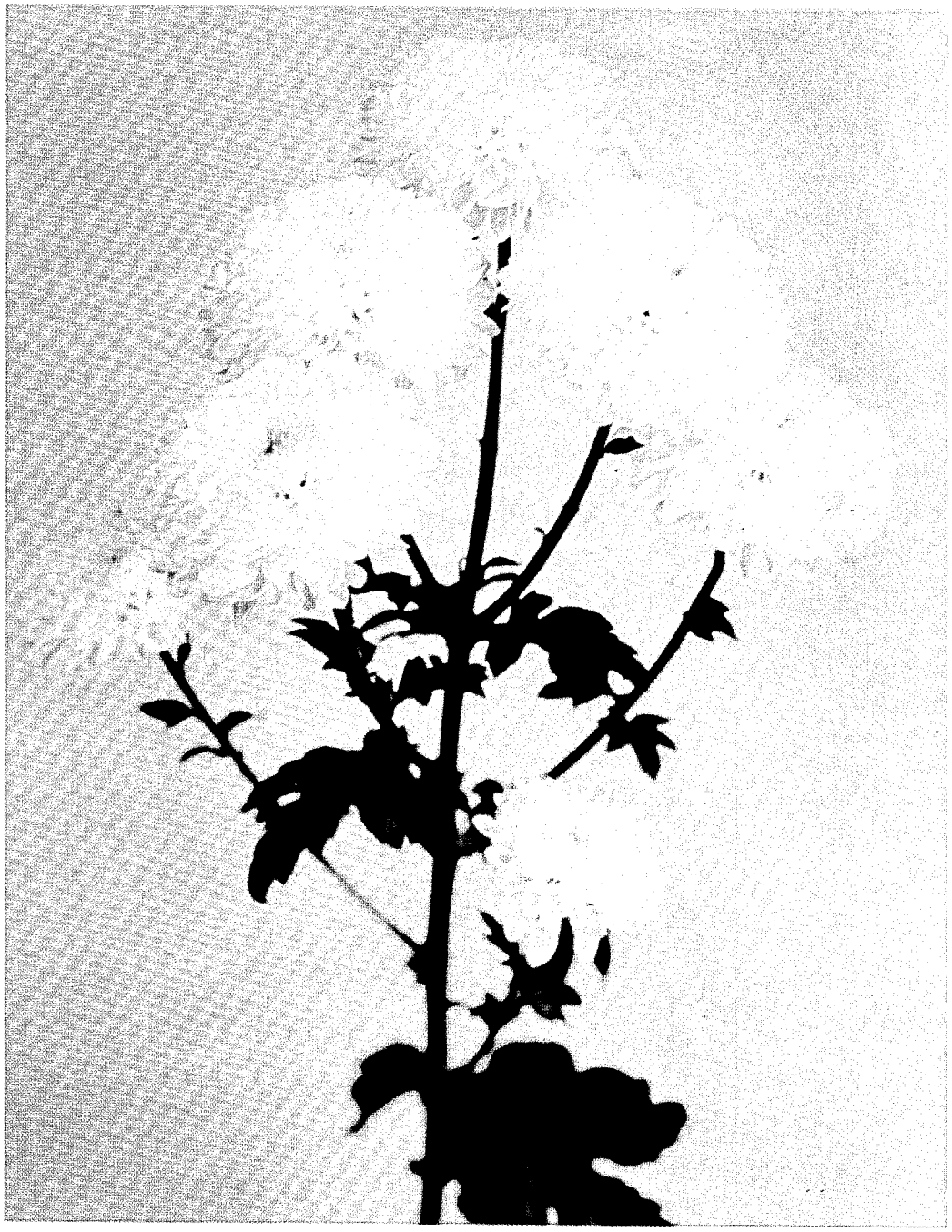

United States Patent Office

Plant Pat. 3,527

Patented Mar. 19, 1974

3,527
CHRYSANTHEMUM PLANT

Walter H. Jessel, Jr., Doylestown, and William E. Duffett, Akron, Ohio, assignors to Yoder Brothers, Inc., Barberton, Ohio

Filed June 19, 1972, Ser. No. 264,305

Int. Cl. A01h *5/00*

U.S. Cl. Plt.—77 1 Claim

The present invention comprises a new and distinct cultivar of chrysanthemum plant which is a seedling of #51448–1 × #63705–1. Both parents are unpatented and identified by the above breeding numbers to distinguish the parents from others in the same breeding program.

The new cultivar is similar in many respects to the well-known, unpatented cultivar Icecap, having the same characteristics of:

(1) Good flowering performance under low light conditions of winter.

(2) Resists shattering.

(3) Approximately the same vigor when both are given the same number of long day weeks prior to the start of short days.

(4) Deeply indented, coarsely serrated foliage.

The new cultivar is distinguished from Icecap by the following characteristics, when grown under comparable conditions:

(1) A longer recommended period of flowering; November through May as compared to December through mid-April for Icecap. It is less thermo-negative than Icecap.

(2) Its ten week response compared to the twelve week response of Icecap.

(3) Flowers approximately one-quarter to one-half inch smaller in diameter.

(4) Approximately two more flowers per stem.

(5) A more green coloration in the center of the flowers.

(6) A flower form which is inclined to be more decorative and less formal than Icecap.

(7) A more coarse texture to the foliage.

The new cultivar was selected from the progeny of the designated cross and when asexually reproduced by cuttings at Barberton, Ohio has been found to retain its distinctive characteristics through successive propagations.

The new cultivar when grown in the vicinity of Barberton, Ohio has a response period of approximately ten weeks, and the following detailed description is based on observations made of the new cultivar in a greenhouse in Barberton, Ohio. The response time, blooming period, color, and total vigor may vary significantly with varying environmental conditions such as temperature, daylength, and light intensity. Suggested flowering in the northern and western United States is from November through May; coastal California, November through May; and Florida, December through March.

The accompanying drawing shows the unique characteristics of the new cultivar, the color being as nearly true as possible with color illustrations of this type. In the following description, color references are made to the Munsell Color Book, 1963 edition, and comparisons are made with the cultivar Icecap. Where only a single value or description appears for the new cultivar, the same value or description applies to the cultivar Icecap.

Bontanical classification: *Chrysanthemum morifolium*

| | Symphony | Icecap |
|---|---|---|
| Bloom: | | |
| Size | 2¼″ | 2½″. |
| Fully expanded | 2½″ | 2¾″. |
| Borne | Cluster (8) on elongated pedicels | Cluster (6) on elongated pedicels. |
| Stems | Strong | |
| Form | Intermediate pom | Formal pom. |
| Permanence | 12–14 days | |
| Color: | | |
| Center of flower | Yellow green, 5GY8/6 | Yellow green, 2.5GY8/6. |
| Base of petals | Yellow green, 2.5GY8/8 | Yellow green, 2.5GY8/8. |
| Inside of petals | Ivory white, 7.5Y9/4 | Light yellow, 10Y9/4 to ivory, 10Y9/1. |
| Reverse of petals | White, N9.5/ | White, N9.5/. |
| Tonality from a distance | Ivory white | Ivory. |
| Discoloration | White, N9.5/ | Ivory, white, 10Y9/1. |
| Petals: | | |
| Texture | Smooth | Smooth. |
| Appearance & form | Open at base broadening to a rounded keel, tapering quickly to a point. | Closed at base, opening slowly to a 3 ridged keel, tapering to a rounded, notched end. |
| Arrangement | Composite, whorled on a single receptacle | |
| Persistence | Resists shatter | |
| Fragrance | Typical chrysanthemum | |
| Reproductive organs: | | |
| Stamen, anthers | None | None to 10. |
| Pollen | do | None to scant. |
| Arrangement | Clustered in center of flower, if present | |
| Styles | Present ray florets | Present both ray and disc florets. |
| Length | Short | |
| Ovaries | At the base of petal attached to receptacle | |
| Plant: | | |
| Form | Herbaceous | |
| Growth | Upright | |
| Height | Approximately 42″–44″ when grown as a single stem winter crop, given 3–4 long day weeks and a total crop time of 13–14 weeks as defined in the timetable of Yoder Brothers, Inc., Barberton, Ohio. | Approximately 42″–44″ when grown as a single stem winter crop given 3–4 long day weeks and a total crop time of 15–16 weeks as defined in the timetable of Yoder Brothers, Inc., Barberton, Ohio. |
| Spread | None when grown single stem, to moderate when pinched | |
| Foliage: | | |
| Top side | Dark green, 7.5GY3/4 | |
| Size | 4¾″ long, 3″ wide | 5½″ long 3″ wide. |
| Quantity | Numerous | |
| Shape | Spatulate lobed | |
| Texture | Coarse | Smooth. |
| Ribs & veins | Prominent | |
| Edge | Deeply indented | |
| Serration | Coarsely serrated | |
| Under side | Light green, 7.5GY5/4 | |
| Stipules | Prominent | Rudimentary at bottom; prominent at top. |

We claim:

1. A new and distinct cultivar of chrysanthemum characterized particularly as to its uniqueness when compared to the cultivar Icecap by its longer recommended period of flowering and its less thermo-negative nature; its ten week response as compared to the twelve week response of Icecap; flowers approximately one-quarter to one-half inch smaller in diameter; approximately two more flowers per stem; a more green coloration in the center of the flowers; a flower form which is more decorative and less formal than Icecap, and by its foliage which is more coarse in texture.

No references cited.

ROBERT E. BAGWILL, Primary Examiner